US00PP11566P

United States Patent [19]

Ruigrok

[11] Patent Number: Plant 11,566

[45] Date of Patent: Oct. 10, 2000

[54] DAHLIA PLANT NAMED 'RUICARO'

[76] Inventor: Frank N. G. Ruigrok, Hyacintenlaan 15, 2182 DE Hillegom, Netherlands

[21] Appl. No.: 09/233,137

[22] Filed: Jan. 19, 1999

[51] Int. Cl.[7] ..... A01H 5/00

[52] U.S. Cl. ..... Plt./321

[58] Field of Search ..... Plt./321

[56] References Cited

U.S. PATENT DOCUMENTS

P.P. 9,846 4/1997 Lommerse ..... Plt./321

*Primary Examiner*—Howard J. Locker

*Assistant Examiner*—Kent L. Bell

*Attorney, Agent, or Firm*—C. A. Whealy

[57] ABSTRACT

A distinct cultivar of Dahlia plant named 'Ruicaro', characterized by its large and numerous double inflorescences that are about 8.5 cm in diameter; intense red ray florets; mostly upright, mounded and uniform growth habit; very dark green shiny leaves; and strong peduncles that hold inflorescences above the foliage.

1 Drawing Sheet

BACKGROUND OF THE INVENTION

The present invention relates to a new and distinct variety of Dahlia plant, botanically known as *Dahlia variabilis*, and hereinafter referred to by the cultivar name 'Ruicaro'.

The new Dahlia is a product of a planned breeding program conducted by the Inventor in Hillegom, The Netherlands. The objective of the breeding program is to develop new compact pot-type Dahlias that are basally branching, freely flowering, and with attractive inflorescence forms and colors.

The new Dahlia originated from a cross made by the Inventor of two unidentified proprietary *Dahlia variabilis* seedling selections in 1992. The cultivar 'Ruicaro' was discovered and selected by the Inventor as a flowering plant within the progeny of the stated cross in a controlled environment in Hillegom, The Netherlands.

Asexual reproduction of the new Dahlia by terminal cuttings harvested in Hillegom, The Netherlands, has shown that the unique features of this Dahlia are stable and reproduced true to type in successive generations.

BRIEF SUMMARY OF THE INVENTION

The new Dahlia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Ruicaro'. These characteristics in combination distinguish 'Ruicaro' as a new and distinct cultivar:

1. Large and numerous double inflorescences that are about 8.5 cm in diameter.

2. Intense red ray florets.

3. Mostly upright, mounded and uniform growth habit.

4. Very dark green shiny leaves.

5. Strong peduncles that hold inflorescences above the foliage.

Compared to plants of the parent cultivars, plants of new Dahlia are shorter, have smaller leaves, and differ in ray floret color.

The new Dahlia is similar in ray floret color to the Dahlia cultivar 'Connie', disclosed in U.S. Plant Pat. No. 6,768. However, in side-by-side comparisons conducted in Hillegom, The Netherlands, plants of the new Dahlia are more compact, are more floriferous and inflorescences are more fully double (have more ray florets per inflorescence) than plants of the cultivar 'Connie'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of the new Dahlia. Ray floret and foliage colors may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in De Lier, The Netherlands, in 12-cm containers in a glass greenhouse with average day and night temperatures of 22° and 18° C., respectively.

Botanical classification: *Dahlia variabilis* 'Ruicaro'.

Parentage:

*Female, or seed, parent.*—Unidentified proprietary *Dahlia variabilis* seedling selection, not patented.

*Male, or pollen, parent.*—Unidentified proprietary *Dahlia variabilis* seedling selection, not patented.

Propagation:

*Type.*—By terminal cuttings or by tissue culture.

*Time to initiate roots.*—Summer: About 5 days at 22° C. Winter: About 8 days at 20° C.

*Time to develop roots.*—Summer: About 12 days at 22° C. Winter: About 16 days at 20° C.

*Rooting habit.*—Easily propagated; roots fine, fibrous and well-branched.

Plant description:

*Appearance.*—Typically grown as potted flowering plants. Mostly upright, mounded and uniform growth habit; rounded plant apex. Moderate growth rate and moderately vigorous. Appropriate for 10 to 12.5-cm containers. Plants typically flower about 8 weeks after planting rooted cuttings. Freely basally branching, however, plants typically require pinching to enhance lateral branch development.

*Plant height*.—About 27 cm.

*Plant spread*.—About 32 cm.

*Stem description*.—Lateral branch diameter: About 1.2 cm. Internode length: About 2.4 cm. Texture: Smooth. Color: 144A.

*Foliage description*.—Arrangement: Young foliage, leaves single; fully expanded foliage, leaves compound, trifoliate; opposite. Leaf length: About 12.4 cm. Leaf width: About 11.3 cm. Terminal leaflet width: About 5.2 cm. Leaflet shape: Ovate. Leaflet apex: Acute. Leaflet base: Attenuate. Leaflet margin: Serrate to dentate. Leaflet texture: Shiny, glabrous. Petiole length: About 5.3 cm. Color: Young leaflets, upper surface: 147A. Young leaflets, lower surface: 147B. Mature leaflets, upper surface: Darker than 147A. Mature leaflets, lower surface: Lighter than 147B. Petiole: 147B.

Flowering description:

*Appearance*.—Double inflorescence form. Inflorescences generally hemispherical and borne on terminals above foliage, arising from leaf axils on strong peduncles; inflorescences above the foliage. Inflorescences face upright and outward. Freely flowering, typically about 20 inflorescences per plant. Disc and ray florets arranged acropetally on a capitulum. Inflorescences are not fragrant.

*Flowering response*.—Under natural conditions, plants flower intermittently from late spring through fall.

*Flower longevity*.—Flowers last about one to two weeks on the plant.

*Flower bud* (*just before opening*).—Shape: Spherical. Length: About 9 mm. Diameter: About 1.2 cm. Color: 145A.

*Inflorescence size*.—Diameter: About 8.5 cm. Depth (height): About 2.2 cm. Disc floret diameter: About 1 cm; conspicuous only on fully opened inflorescences.

*Ray florets*.—Quantity per inflorescence: About 55. Shape: Broadly elliptic. Orientation: Initially upright to horizontal; cupped. Length: About 4.2 cm. Width: About 2.1 cm. Apex: Acute or emarginate. Base: Attenuate. Margin. Entire. Texture: Satiny, glabrous. Color: When opening, upper surface: 46A. When opening, lower surface: 46A to 42A with yellowish, close to 10A, longitudinal veins. Fully opened, upper surface: More intense than 45A. Fully opened, lower surface: 42A or slightly darker with yellowish, 10B, longitudinal veins.

*Disc florets*.—Quantity per inflorescence: About 35. Shape: Tubular. Orientation: Upright. Length: About 1.2 cm. Width: Apex, about 1.5 mm; base, about 1 mm. Apex: Dentate. Color: Apex, 12A; mid-section and base, whitish green.

*Peduncle*.—Aspect: Upright and strong. Length: About 10 cm. Diameter: About 4 mm. Texture: Smooth. Color: 144A.

*Involucral bracts*.—Shape: Oblong. Tip: Rounded. Margin: Entire. Texture: Waxy. Color: 144A to 144C.

*Reproductive organs*.—Androecium (Present on disc florets): Anther color: 9A. Pollen amount: Moderate to abundant. Pollen color: 17A. Gynoecium present on ray and disc florets.

Disease resistance: Resistance to known Dahlia diseases has not been observed on plants grown under commercial greenhouse conditions.

Seed production: Seed production has not been observed.

It is claimed:

1. A new and distinct cultivar of Dahlia plant named 'Ruicaro', as illustrated and described.

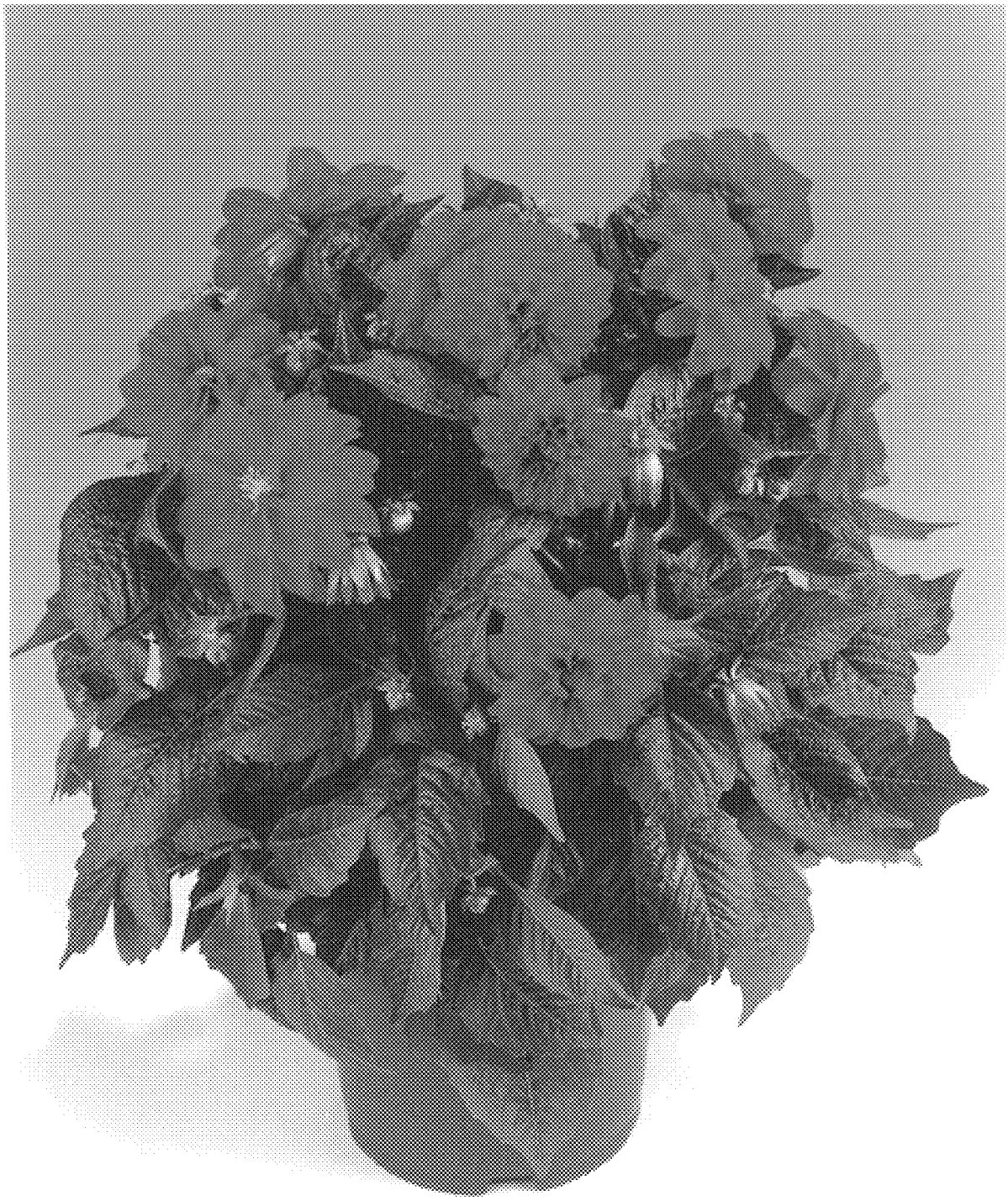

* * * * *